United States Patent
Sosna et al.

(10) Patent No.: US 6,790,910 B1
(45) Date of Patent: Sep. 14, 2004

(54) ANTIMICROBIAL ADDITIVES

(75) Inventors: Friedrich Sosna, Dorsten (DE); Peter Ottersbach, Windeck (DE); Beate Kossmann, Hagen (DE)

(73) Assignee: CREAVIS Gesellschaft fuer Technologie und Innovation mbH, Marl (DE)

( * ) Notice: Subject to any disclaimer, the term of this patent is extended or adjusted under 35 U.S.C. 154(b) by 0 days.

(21) Appl. No.: 10/070,817
(22) PCT Filed: Jul. 8, 2000
(86) PCT No.: PCT/EP00/06501
  § 371 (c)(1),
  (2), (4) Date: Mar. 11, 2002
(87) PCT Pub. No.: WO01/18077
  PCT Pub. Date: Mar. 15, 2001

(30) Foreign Application Priority Data

Sep. 9, 1999 (DE) .......................... 199 43 182
May 9, 2000 (DE) .......................... 100 22 453

(51) Int. Cl.$^7$ .......................... C08L 23/00; C08L 23/04; C08L 33/24; C08L 35/02; C08L 25/02
(52) U.S. Cl. .......................... 525/191; 525/206; 525/217; 525/218; 525/222; 525/239; 525/240; 525/241
(58) Field of Search .......................... 525/191, 206, 525/217, 218, 222, 239, 240, 241

(56) References Cited

U.S. PATENT DOCUMENTS

| | | | |
|---|---|---|---|
| 5,967,714 A | 10/1999 | Ottersbach et al. | |
| 6,096,800 A | 8/2000 | Ottersbach et al. | |
| 6,203,856 B1 | 3/2001 | Ottersbach et al. | |

FOREIGN PATENT DOCUMENTS

| | | |
|---|---|---|
| DE | 197 15 426 | 10/1998 |
| EP | 0 096 250 | 12/1983 |
| EP | 0 814 105 | 12/1997 |
| EP | 0 862 859 | 9/1998 |
| EP | 0 949 284 | 10/1999 |
| FR | 2 757 866 | 7/1998 |

OTHER PUBLICATIONS

U.S. patent application Ser. No. 10/070,817, Sosna et al., filed Mar. 11, 2002.
U.S. patent application Ser. No. 10/211,373, Ottersbach et al., filed Aug. 5, 2002.
U.S. patent application Ser. No. 10/244,163, Ottersbach et al., filed Sep. 16, 2002.
U.S. patent application Ser. No. 10/469,534, Ottersbach et al., filed Sep. 8, 2003.
U.S. patent application Ser. No. 10/432,630, Ottersbach et al., filed Jun. 9, 2003.
U.S. patent application Ser. No. 10/466,710, Ottersbach et al., filed Jul. 17, 2003.
U.S. patent application Ser. No. 10/645,553, Ottersbach et al., filed Aug. 22, 2003.

*Primary Examiner*—Nathan M. Nutter
(74) *Attorney, Agent, or Firm*—Oblon, Spivak, McClelland, Maier & Neustadt, P.C.

(57) ABSTRACT

The invention relates to antimicrobial polymers and polymer blends which are prepared by polymerizing a monomer of the formula I:

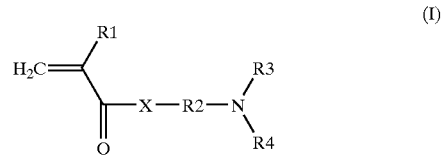

where

R1=—H or —CH$_3$

R2=branched or unbranched aliphatic hydrocarbon radical having from 1 to 5 carbon atoms, R3=H, or branched or unbranched aliphatic hydrocarbon radical having from 1 to 7 carbon atoms, R4=H, or branched or unbranched aliphatic hydrocarbon radical having from 1 to 7 carbon atoms, R5=H, or branched or unbranched aliphatic hydrocarbon radical having from 1 to 7 carbon atoms, and

X=O, NH, NR5 and, where appropriate, then mixing with at least one other polymer.

The antimicrobial polymers or blends may be used for producing hygiene items or items for medical technology, e.g. as a coating, or else in surface coatings or protective paints. They may also be used in a process for eliminating/reducing biofouling in water systems.

11 Claims, No Drawings

ANTIMICROBIAL ADDITIVES

The invention relates to antimicrobial polymers obtained by polymerizing acryloxyalkylamines. The invention further relates to a process for preparing these antimicrobial polymers and to their use.

It is highly undesirable for bacteria to become established or to spread on the surfaces of piping, or of containers or packaging. Slime layers frequently form and permit sharp rises in microbial populations, and these can lead to persistent impairment of the quality of water, drinks or foods, and even to spoilage of the product and harm to the health of consumers.

Bacteria must be kept away from all fields of life where hygiene is important. This affects textiles for direct body contact, especially in the genital area, and those for the care of the elderly or sick. Bacteria must also be kept away from surfaces of the furniture and equipment used in patient-care areas, especially in areas for intensive care or neonatal care, and in hospitals, especially in the areas where medical intervention takes place, and in isolation wards for critical cases of infection, and also in toilets.

A current method of treating equipment, or the surfaces of furniture or of textiles, to resist bacteria either when this becomes necessary or else as a precautionary measure, is to use chemicals or solutions or mixtures of these which are disinfectants and therefore have fairly broad general antimicrobial action. Chemical agents of this type act nonspecifically and are frequently themselves toxic or irritant, or form degradation products which are hazardous to health. In addition, people frequently exhibit intolerance to these materials once they have become sensitized.

Another method of counteracting surface spread of bacteria is to incorporate substances with antimicrobial action into a matrix.

U.S. Pat. No. 4,532,269, for example, discloses a terpolymer made from butyl methacrylate, tributyltin methacrylate, and tert-butylaminoethyl methacrylate. This copolymer is used as an antimicrobial paint for ships, and the hydrophilic tert-butylaminoethyl methacrylate present promotes gradual erosion of the polymer and thus releases the highly toxic tributyltin methacrylate, which is the antimicrobial active ingredient.

In these applications, the copolymer prepared with aminomethacrylates is merely a matrix or carrier for added microbicidal ingredients which can diffuse or migrate out of the carrier material. Sooner or later, polymers of this type loose their activity, once the necessary minimum inhibitor concentration (MIC) at the surface has been lost.

The European patent application 0 862 858 has also disclosed that copolymers of tert-butylaminoethyl methacrylate, a methacrylate with a secondary amino function, has inherent microbicidal properties. Systems developed in the future will again have to be based on novel compositions with improved effectiveness if undesirable resistance phenomena in the microbes are to be avoided, particularly bearing in mind the microbial resistance known from antibiotics research.

The object on which the present invention was based was therefore to develop novel antimicrobial polymers. When used as a coating or covering material, these should prevent bacteria from colonizing surfaces and spreading thereon.

Surprisingly, it has now been found that homopolymerization of acryloxyalkylamines or of methacryloxyalkylamines gives polymers which are lastingly microbicidal, are not damaged by solvents or physical stresses, and exhibit no migration. There is no need here for the use of other biocidal active ingredients. The surface of the polymers is, of course, important for the antimicrobial action of these homopolymers.

The present invention therefore provides antimicrobial polymers which are obtained by polymerizing a monomer of the formula I:

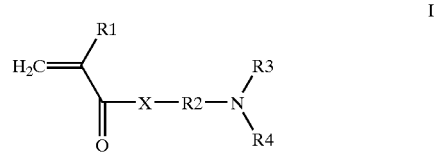

where
R1=—H or —CH$_3$
R2=branched or unbranched aliphatic hydrocarbon radical having from 1 to 5 carbon atoms,
R3=H, or branched or unbranched aliphatic hydrocarbon radical having from 1 to 7 carbon atoms,
R4=H, or branched or unbranched aliphatic hydrocarbon radical having from 1 to 7 carbon atoms,
R5=H, or branched or unbranched aliphatic hydrocarbon radical having from 1 to 7 carbon atoms, and
X=O, NH, NR5.

Acryloyloxyalkylamines (X=O) and alkylaminoacrylamides (X=NH) are particularly suitable for preparing the polymers of the invention.

The radicals R3 and R4 may be identical or different. If R3 and/or R4 are hydrocarbon groups, these may in particular be methyl, ethyl, isopropyl, n-propyl, or tert-butyl groups.

Preferred monomers used of the formula I are 2-tert-butylaminoethyl methacrylate, 2-diethylaminoethyl methacrylate, 2-dimethylaminomethyl methacrylate, 2-tert-butylaminoethyl acrylate, 3-dimethylaminopropyl acrylate, 2-diethylaminoethyl acrylate, 2-dimethyl-aminoethyl acrylate, N-3-dimethylaminopropylmeth-acrylamide, N-3-diethylaminopropylmethacrylamide, N-3-dimethylaminopropylacrylamide, or N-3-diethylaminopropylacrylamide.

The antimicrobial polymers of the invention may be obtained by homopolymerizing monomers of the formula I. The free-radical polymerization advantageously takes place by a chemical route by way of a free-radical initiator, or initiated by radiation. The examples describe typical procedures.

The present invention further provides antimicrobial polymer blends which are prepared by mixing one or more antimicrobial polymers each obtainable by polymerizing monomers of the formula I, where R1, R2, R3, R4, R5 and X are as defined above, with at least one other polymer.

Examples of blend material, i.e. other polymer with which the polymer of the invention is mixed, are polyurethanes, PVC, polyolefins, such as polyethylene or polypropylene, polysiloxanes, polystyrenes, polyacrylates, polymethacrylates, and engineering plastics, e.g. polyamides or polyterephthalates. To obtain adequate antimicrobial action of a polymer blend, the proportion of the antimicrobial polymer of the invention should be from 0.2 to 90% by weight, preferably from 40–90% by weight.

In principle, any of the processes known in the art, for example as described in detail by H.-G. Elias, Makromole-kUle [Macromolecules], Vol. 2, 5th edition, pp. 620 et seq., may be used to prepare the antimicrobial polymer blends. For example, two previously formed polymers are mixed in the melt by mixing the pelletized or pulverulent polymers on roll mills, in kneaders, or using extruders. In the case of thermoplastics, this is achieved by heating above the glass transition temperatures or melting points. In the case of solution mixing, the starting materials are separately prepared solutions of the two polymers in the same solvent.

In specific embodiments of the present invention, it is possible for the proportion of the one or more antimicrobial polymers of the invention in a blend to be less than 40–90% by weight, e.g. from 0.2 to 70% by weight, preferably from 0.2 to 30% by weight, particularly preferably from 0.2 to 15% by weight, very particularly preferably from 0.2 to 10% by weight.

One preferred process for preparing the antimicrobial polymers and, respectively, polymer blends of the invention is free-radical polymerization of monomers of the formula I in solution, using a free-radical initiator. The resultant antimicrobial polymers may, where appropriate after mixing with other polymers, be applied to a surface by known methods, such as dipping, spraying, or spreading. Solvents which have proven successful are ethanol, methanol, water/alcohol mixtures, methyl ethyl ketone, diethyl ether, dioxane, hexane, heptane, benzene, toluene, chloroform, dichloromethane, tetrahydrofuran, and acetonitrile, but it is also possible to use other solvents as long as they have sufficient capability for dissolving the polymers and give good wetting of the substrate surfaces. Solutions with polymer contents of from 3 to 20% by weight, for example about 5% by weight, have proven successful in practice and generally give, in a single pass, coherent coatings which cover the substrate surface and may have a thickness of more than 0. 1 $\mu$m.

It is also possible for the antimicrobial polymers and, respectively, polymer blends of the invention to be in the form of a melt when applied to the substrates, e.g. by coextrusion, or by way of dipping, spraying, or surface-coating.

The antimicrobial polymers and, respectively, polymers blends of the invention may moreover also be used as additives or components for formulating polymer blends, inks or paints, surface coatings, or biocides.

In the case of the polymer blends, a particularly advantageous method is compounding by way of extrusion, where appropriate also by way of coextrusion with other polymers.

If polymers or, respectively, polymer blends of the invention are used as an additive or component in inks or paints, surface coatings, or biocides, much lower concentrations may be sufficient, e.g. in the range of a few parts per hundred or per thousand.

Use of the Modified Polymer Substrates

The present invention further provides the use of the antimicrobial polymers and, respectively, polymer blends of the invention for producing antimicrobial products, and the resultant products per se. The products may comprise antimicrobial polymers of the invention or consist of these. Products of this type are preferably based on polyamides, on polyurethanes, on polyether block amides, on polyesteramides or -imides, on PVC, on polyolefins, on silicones, on polysiloxanes, on polymethacrylate, or on polyterephthalates, which have surfaces coated with polymers of the invention or have been processed using polymers of the invention, in the form of a polymer blend.

Examples of antimicrobial products of this type are machine parts for processing food and drink, components in air conditioning systems, roofing, items for bathroom and toilet use, kitchen items, components for sanitary installations, components of animal cages or of animal houses, recreational products for children, components of water systems, packaging for food or drink, operator units (touch panels) of devices, and contact lenses.

The polymers and, respectively, polymer blends of the invention may be used anywhere where importance is placed on surfaces which are as free as possible from bacteria, i.e. are microbicidal, or on surfaces with release properties. Examples of applications of the polymers and, respectively, polymer blends of the invention are in particular surface coatings, protective paints, and other coatings in the following sectors:

marine: boat hulls, docks, buoys, drilling platforms, ballast water tanks construction: roofing, basements, walls, facades, greenhouses, sun protection, garden fencing, wood protection, tent roof material, fabrics sanitary: public conveniences, bathrooms, shower curtains, toilet items, swimming pools, saunas, jointing, sealing compounds requisites for daily life: machines, kitchen, kitchen items, sponge pads, recreational products for children, packaging for food or drink, milk processing, drinking water systems, cosmetics machine parts: air conditioning systems, ion exchangers, process water, solar-powered units, heat exchangers, bioreactors, membranes medical technology: contact lenses, diapers, membranes, implants consumer articles: automobile seats, clothing (socks, sports clothing), hospital equipment, door handles, telephone handsets, public conveyances, animal cages, cash registers, carpeting, wallpapers.

The polymers and, respectively, polymer blends may likewise be used as an additive for surface coatings in the maritime sector, in particular for eliminating larval barnacles on boat hulls, and generally as an additive in antifouling paints, particularly in sea water in which salt is present.

The antimicrobial polymers and, respectively, polymer blends of the invention may also be used as additives in formulating cosmetic products, e.g. for pastes or ointments. Here the proportion of polymers or, respectively, polymer blends of the invention may be lowered as fat as relatively small numbers of parts per hundred or parts per thousand, depending on the activity of the polymer and the formulation.

The polymers and, respectively, polymer blends of the invention are also used as a biofouling inhibitor in cooling circuits. To prevent damage to cooling circuits by infestation with algae or bacteria, the circuits would have to be cleaned frequently or appropriately oversized. In open cooling systems, as are usually found in power plants and in chemical plants, the addition of microbicidal substances such as formalin is not possible. Other microbicidal substances are frequently highly corrosive or form foams, preventing their use in systems of this type.

In contrast, the inventive polymers or blends of these with the other polymers mentioned may be fed in finely dispersed form into the process water. The bacteria are killed on contact with the antimicrobial polymers and, if necessary, removed from the system by filtering off the dispersed polymer/blend. Deposits of bacteria or algae on sections of the plant can thus effectively be prevented. The result of this is a completely novel process for eliminating or reducing biofouling in process water systems.

The present invention therefore also provides processes for sterilizing cooling water streams, by adding antimicrobial polymers or polymer blends of these in dispersed form to the cooling water. For the purposes of the present invention, cooling water includes any process water stream which is used for heating or cooling purposes in closed or open circulating systems.

The dispersed form of the copolymers or of their blends may be obtained within the preparation process itself, for example by emulsion polymerization, precipitation polymerization, or suspension polymerization, or subsequently by comminuting, e.g. in a jet mill. The size distribution of the resultant particles when they are used is preferably from 0.001 to 3 mm (diameter of particles), firstly providing a large surface for killing the bacteria or algae and secondly enabling, if required, ready separation from the cooling water, e.g. by filtration. One way of working the process is to remove from the system continuously a proportion (5 to 10%) of the copolymers/blends used and to replace it with an appropriate amount of fresh material. As an alternative, the number of microbes in the water may be checked, and further antimicrobial copolymer/blend added as required. Depending on the quality of the water, it is sufficient to use from 0.1 to 100 g of antimicrobial copolymer or blends of these per $m^3$ of cooling water.

The present invention also provides the use for producing hygiene products or items for medical technology, of the polymer substrates modified on the surface using polymers or, respectively, polymer blends of the invention. The statements above concerning preferred materials are again applicable. Examples of hygiene products of this type are toothbrushes, toilet seats, combs, and packaging materials. For the purposes of the present invention, hygiene items also include articles which can come into contact with many people, for example telephone handsets, stair rails, door handles, window catches, and also grab straps and grab handles in public conveyances. Examples of items for medical technology are catheters, tubing, protective or backing films, and also surgical instruments.

The uses mentioned for the antimicrobial polymers also apply to the polymer blends of the invention.

The examples below are given for further description of the present invention, but are not intended to limit the scope of the invention as set out in the claims.

EXAMPLE 1

60 ml of 2-diethylaminoethyl methacrylate (Aldrich) and 250 ml of ethanol are charged to a three-necked flask and heated to 65° C. under a stream of argon. 0.74 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours.

EXAMPLE 1a 0.05 g of the product from example 1 is shaken in 20 ml of a test microbial suspension of *Staphylococcus aureus*. After a contact time of 15 minutes, 1 ml of the test microbial suspension is removed, and the number of microbes in the test mixture is determined. After expiry of this time, no remaining *Staphylococcus aureus* microbes are detectable.

EXAMPLE 1b 0.05 g of the product from example 1 is shaken in 20 ml of a test microbial suspension of *Pseudomonas aeruginosa*. After a contact time of 60 minutes, 1 ml of the test microbial suspension is removed, and the number of microbes in the test mixture is determined. After expiry of this time, the number of microbes has fallen from $10^7$ to $10^3$.

EXAMPLE 2

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours.

EXAMPLE 2a 0.05 g of the product from example 2 is shaken in 20 ml of a test microbial suspension of *Staphylococcus aureus*. After a contact time of 15 minutes, 1 ml of the test microbial suspension is removed, and the number of microbes in the test mixture is determined. After expiry of this time, no remaining *Staphylococcus aureus* microbes are detectable.

EXAMPLE 2b 0.05 g of the product from example 2 is shaken in 20 ml of a test microbial suspension of *Pseudomonas aeruginosa*. After a contact time of 60 minutes, 1 ml of the test microbial suspension is removed, and the number of microbes in the test mixture is determined. After expiry of this time, the number of microbes has fallen from $10^7$ to $10^2$.

EXAMPLE 3

20 ml of N-3-dimethylaminopropylacrylamide (Aldrich) and 70 ml of ethanol are charged to a three-necked flask and heated to 65° C. under a stream of argon. 0.2 g of azobisisobutyronitrile dissolved in 5 ml of ethyl methyl ketone is then slowly added dropwise, with stirring. The mixture is heated to 70° C. and stirred at this temperature for 72 hours. After expiry of this time, the reaction mixture is stirred into 0.5 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours.

EXAMPLE 3a 0.05 g of the product from example 3 is shaken in 20 ml of a test microbial suspension of *Staphylococcus aureus*. After a contact time of 15 minutes, 1 ml of the test microbial suspension is removed, and the number of microbes in the test mixture is determined. After expiry of this time, the number of microbes has fallen from $10^7$ to $10^3$.

EXAMPLE 3b 0.05 g of the product from example 3 is shaken in 20 ml of a test microbial suspension of *Pseudomonas aeruginosa*. After a contact time of 60 minutes, 1 ml of the test microbial suspension is removed, and the number of microbes in the test mixture is determined. After expiry of this time, the number of microbes has fallen from $10^7$ to $10^3$.

EXAMPLE 4

10 g of the polymer from example 1 are heated to 165° C. This heated polymer is then mixed with 3 g of polymethyl methacrylate (Aldrich) which had likewise been heated in advance to 165° C. The two polymers are very thoroughly mixed and cooled to room temperature at a rate of 20° C. per hour.

EXAMPLE 4a 0.05 g of the product from example 4 is shaken in 20 ml of a test microbial suspension of *Staphylococcus aureus*. After a contact time of 15 minutes, 1 ml of the test microbial suspension is removed, and the number of microbes in the test mixture is determined. After expiry of this time, the number of microbes has fallen from $10^7$ to $10^3$.

EXAMPLE 4b 0.05 g of the product from example 4 is shaken in 20 ml of a test microbial suspension of *Pseudomonas aeruginosa*. After a contact time of 60 minutes, 1 ml of the test microbial suspension is removed, and the number of microbes in the test mixture is determined. After expiry of this time, the number of microbes has fallen from $10^7$ to $10^4$.

EXAMPLE 5

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 5 g of the product are dissolved in 32 g of diisononyl phthalate. 64 g of polyvinyl chloride pellets are then added to this mixture, and the mixture is intimately mixed until it becomes a paste. 20 g of the resultant paste are applied to a metal sheet, using a doctor, in such a way as to give a layer of 0.7 mm thickness. The sheet covered by the paste is then heated to 200° C. for 2 minutes, whereupon the paste gels, giving a plasticized PVC film.

EXAMPLE 5a

A piece of the plasticized PVC film from example 5, dimensions 3×3 cm, is placed on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 5b

A piece of the plasticized PVC film from example 5, dimensions 3×3 cm, is placed on the base of a glass beaker which contains 20 ml of a test microbial suspension of *Pseudomonas aeruginosa*, and is subjected to shaking. After a contact time of 4 hours, 1 ml of the test microbial suspension is removed, and the number of microbes in the test mixture is determined. After expiry of this time, no remaining *Staphylococcus aureus* microbes are detectable.

EXAMPLE 6

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are dissolved in 32 g of diisononyl phthalate. 64 g of polyvinyl chloride pellets are then added to this mixture, and the mixture is intimately mixed until it becomes a paste. 20 g of the resultant paste are applied to a metal sheet, using a doctor, in such a way as to give a layer of 0.7 mm thickness. The sheet covered by the paste is then heated to 200° C. for 2 minutes, whereupon the paste gels, giving a plasticized PVC film.

EXAMPLE 6a

A piece of the plasticized PVC film from example 6, dimensions 3×3 cm, is placed on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 6b

A piece of the plasticized PVC film from example 6, dimensions 3×3 cm, is placed on the base of a glass beaker which contains 20 ml of a test microbial suspension of *Pseudomonas aeruginosa*, and is subjected to shaking. After a contact time of 4 hours, 1 ml of the test microbial suspension is removed, and the number of microbes in the test mixture is determined. After expiry of this time, the number of microbes has fallen from $10^7$ to $10^3$.

EXAMPLE 7

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 5 g of the product are stirred into 95 g of Rowacryl G-31293 acrylic surface coating from the company ROWA.

EXAMPLE 7a

Using a brush, an aluminum sheet of dimensions 5×5 cm is painted with the acrylic surface coating from example 7 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 7b

Using a brush, an aluminum sheet of dimensions 5×5 cm is painted with the acrylic surface coating from example 7 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, no remaining *Pseudomonas aeruginosa* microbes are detectable.

EXAMPLE 8

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are stirred into 98 g of Rowacryl G-31293 acrylic surface coating from the company ROWA.

EXAMPLE 8a

Using a brush, an aluminum sheet of dimensions 5×5 cm is painted with the acrylic surface coating from example 8 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 8b

Using a brush, an aluminum sheet of dimensions 5×5 cm is painted with the acrylic surface coating from example 8 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^3$.

EXAMPLE 9

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 5 g of the product are stirred into 95 g of Plextol D 510 from the company PolymerLatex, an aqueous dispersion of a methacrylate-acrylate copolymer.

EXAMPLE 9a

Using a brush, an aluminum sheet of dimensions 5×5 cm is painted with the dispersion from example 9 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 9b

Using a brush, an aluminum sheet of dimensions 5×5 cm is painted with the dispersion from example 9 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^2$.

EXAMPLE 10

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are stirred into 98 g of Plextol D 510 from the company PolymerLatex, an aqueous dispersion of a methacrylate-acrylate copolymer.

EXAMPLE 10a

Using a brush, an aluminum sheet of dimensions 5×5 cm is painted with the dispersion from example 10 and then dried for 24 hours at 35° C. in a drying cabinet. This aluminum sheet is placed, with its coated side upward, on the base of a glass beaker which contains 20 ml of a test microbial suspension of Staphylococcus aureus, and is subjected to shaking. After a contact time of 2 hours, 1 ml of the test microbial suspension is removed, and the number of microbes in the test mixture is determined. After expiry of this time, no remaining Staphylococcus aureus microbes are detectable.

EXAMPLE 10b

Using a brush, an aluminum sheet of dimensions 5×5 cm is painted with the dispersion from example 10 and then dried for 24 hours at 35° C. in a drying cabinet. This aluminum sheet is placed, with its coated side upward, on the base of a glass beaker which contains 20 ml of a test microbial suspension of Pseudomonas aeruginosa, and is subjected to shaking. After a contact time of 2 hours, 1 ml of the test microbial suspension is removed, and the number of microbes in the test mixture is determined. After expiry of this time, the number of microbes has fallen from $10^7$ to $10^2$.

EXAMPLE 11

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 1 g of the product is dissolved in 99 g of ethanol. Six cotton pads, each of diameter 3 cm, are immersed for 1 second into this solution, removed, and dried at room temperature for 24 hours.

EXAMPLE 11a

Cotton pads from example 11 are inoculated with, respectively, Chlorella sp., Trentepohlia sp., Gloeocapsa sp., Calothrix sp., and Aspergillus niger.

These specimens are then placed in an incubator for 3 weeks. Unlike control specimens run simultaneously, no growth is detectable on any of the coated absorbent cotton pads.

EXAMPLE 12

60 ml of 2-diethylaminoethyl methacrylate (Aldrich) and 250 ml of ethanol are charged to a three-necked flask and heated to 65° C. under a stream of argon. 0.74 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 12a

The aluminum sheet from example 12 is placed, with its coated side upward, on the base of a glass beaker which contains 20 ml of a test microbial suspension of Staphylococcus aureus, and subjected to shaking. After a contact time of 2 hours, 1 ml of the test microbial suspension is removed, and the number of microbes in the test mixture is determined. After expiry of this time, no remaining Staphylococcus aureus microbes are detectable.

EXAMPLE 12b

The aluminum sheet from example 12 is placed, with its coated side upward, on the base of a glass beaker which contains 20 ml of a test microbial suspension of Staphylococcus aureus, and subjected to shaking. After a contact time of 4 hours, 1 ml of the test microbial suspension is removed, and the number of microbes in the test mixture is determined. After expiry of this time, no remaining Pseudomonas aeruginosa microbes are detectable.

EXAMPLE 13

90 ml of 2-tert-butylaminoethyl methacrylate (Aldrich) and 180 ml of ethanol are charged to a three-necked flask and heated to 65° C. under a stream of argon. 0.745 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1 l of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 13a

The aluminum sheet from example 13 is placed, with its coated side upward, on the base of a glass beaker which contains 20 ml of a test microbial suspension of Staphylococcus aureus, and subjected to shaking. After a contact time of 2 hours, 1 ml of the test microbial suspension is removed, and the number of microbes in the test mixture is determined. After expiry of this time, no remaining Staphylococcus aureus microbes are detectable.

EXAMPLE 13b

The aluminum sheet from example 13 is placed, with its coated side upward, on the base of a glass beaker which contains 20 ml of a test microbial suspension of Staphylococcus aureus, and subjected to shaking. After a contact time of 4 hours, 1 ml of the test microbial suspension is removed, and the number of microbes in the test mixture is determined. After expiry of this time, no remaining Pseudomonas aeruginosa microbes are detectable.

EXAMPLE 14

20 ml of 3-dimethylaminopropyl acrylate (Aldrich) and 70 ml of ethanol are charged to a three-necked flask and heated to 65° C. under a stream of argon. 0.2 g of azobisisobutyronitrile dissolved in 5 ml of ethyl methyl ketone is then slowly added dropwise, with stirring. The mixture is heated to 70° C. and stirred at this temperature for 72 hours. After expiry of this time, the reaction mixture is stirred into 0.5 1 of demineralized water, whereupon the polymeric product precipitates. After separation of the product by filtration, the filter residue is washed with 100 ml of a 10% strength solution of ethanol in water in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 14a

The aluminum sheet from example 14 is placed, with its coated side upward, on the base of a glass beaker which contains 20 ml of a test microbial suspension of *Staphylococcus aureus*, and subjected to shaking. After a contact time of 4 hours, 1 ml of the test microbial suspension is removed, and the number of microbes in the test mixture is determined. After expiry of this time, no remaining *Staphylococcus aureus* microbes are detectable.

EXAMPLE 14b

The aluminum sheet from example 14 is placed, with its coated side upward, on the base of a glass beaker which contains 20 ml of a test microbial suspension of *Pseudomonas aeruginosa*, and subjected to shaking. After a contact time of 8 hours, 1 ml of the test microbial suspension is removed, and the number of microbes in the test mixture is determined. After expiry of this time, no remaining *Pseudomonas aeruginosa* microbes are detectable.

EXAMPLE 15

10 g of the polymer from example 1 are heated to 165° C. This heated polymer is then mixed with 3 g of polymethyl methacrylate (Aldrich) which had likewise been heated in advance to 165° C. The two polymers are very thoroughly mixed, applied to an aluminum sheet with a thickness of 0.5 cm and dimensions 2×2 cm, and cooled to room temperature at a rate of 20° C. per hour.

EXAMPLE 15a

The aluminum sheet from example 15 is placed, with its coated side upward, on the base of a glass beaker which contains 20 ml of a test microbial suspension of *Staphylococcus aureus*, and subjected to shaking. After a contact time of 4 hours, 1 ml of the test microbial suspension is removed, and the number of microbes in the test mixture is determined. After expiry of this time, no remaining *Staphylococcus aureus* microbes are detectable.

EXAMPLE 15b

The aluminum sheet from example 15 is placed, with its coated side upward, on the base of a glass beaker which contains 20 ml of a test microbial suspension of *Pseudomonas aeruginosa*, and subjected to shaking. After a contact time of 8 hours, 1 ml of the test microbial suspension is removed, and the number of microbes in the test mixture is determined. After expiry of this time, no remaining *Pseudomonas aeruginosa* microbes are detectable.

EXAMPLE 16

50 ml of dimethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 1 of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 16a

The aluminum sheet from example 16 is placed, with its coated side upward, on the base of a glass beaker which contains 20 ml of a test microbial suspension of *Staphylococcus aureus*, and subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 16b

The aluminum sheet from example 16 is placed, with its coated side upward, on the base of a glass beaker which contains 20 ml of a test microbial suspension of *Pseudomonas aeruginosa*, and subjected to shaking. After a contact time of 4 hours, 1 ml of the test microbial suspension is removed, and the number of microbes in the test mixture is determined. After expiry of this time, the number of microbes has fallen from $10^7$ to $10^3$ microbes per ml.

EXAMPLE 17

50 ml of diethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 1 of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 17a

The aluminum sheet from example 17 is placed, with its coated side upward, on the base of a glass beaker which contains 20 ml of a test microbial suspension of *Staphylococcus aureus*, and subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 17a

The aluminum sheet from example 17 is placed, with its coated side upward, on the base of a glass beaker which contains 20 ml of a test microbial suspension of *Pseudomonas aeruginosa*, and subjected to shaking. After a contact time of 4 hours, 1 ml of the test microbial suspension is removed, and the number of microbes in the test mixture is determined. After expiry of this time, the number of microbes has fallen from $10^7$ to $10^3$ microbes per ml.

EXAMPLE 18

45-ml of N-3-dimethylaminopropylacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are dissolved in 10 g of tetrahydrofuran and applied, using a 100 micrometer doctor, to an aluminum sheet of 0.5 cm thickness and dimensions 2×2 cm. The sheet is then dried for 24 hours at 50° C.

EXAMPLE 18a

The aluminum sheet from example 18 is placed, with its coated side upward, on the base of a glass beaker which contains 20 ml of a test microbial suspension of *Staphylococcus aureus*, and subjected to shaking. After a contact time of 4 hours, 1 ml of the test microbial suspension is removed, and the number of microbes in the test mixture is determined. After expiry of this time, no remaining *Staphylococcus aureus* microbes are detectable.

EXAMPLE 18b

The aluminum sheet from example 18 is placed, with its coated side upward, on the base of a glass beaker which contains 20 ml of a test microbial suspension of *Pseudomonas aeruginosa*, and subjected to shaking. After a contact time of 8 hours, 1 ml of the test microbial suspension is removed, and the number of microbes in the test mixture is determined. After expiry of this time, the number of microbes has fallen from $10^7$ to $10^4$ microbes per ml.

EXAMPLE 19

10 g of the polymer from example 16 are heated to 165° C. This heated polymer is then mixed with 3 g of polymethyl methacrylate (Aldrich) which had likewise been heated in advance to 165° C. The two polymers are very thoroughly mixed, applied to an aluminum sheet with a thickness of 0.5 cm and dimensions 2×2 cm, and cooled to room temperature at a rate of 20° C. per hour.

EXAMPLE 19a

The aluminum sheet from example 19 is placed, with its coated side upward, on the base of a glass beaker which contains 20 ml of a test microbial suspension of *Staphylococcus aureus*, and subjected to shaking. After a contact time of 4 hours, 1 ml of the test microbial suspension is removed, and the number of microbes in the test mixture is determined. After expiry of this time, no remaining *Staphylococcus aureus* microbes are detectable.

EXAMPLE 19b

The aluminum sheet from example 19 is placed, with its coated side upward, on the base of a glass beaker which contains 20 ml of a test microbial suspension of *Pseudomonas aeruginosa*, and subjected to shaking. After a contact time of 8 hours, 1 ml of the test microbial suspension is removed, and the number of microbes in the test mixture is determined. After expiry of this time, the number of microbes has fallen from $10^7$ to $10^4$ microbes per ml.

EXAMPLE 20

50 ml of dimethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 6 g of the product are dissolved in 32 g of diisononyl phthalate. 64 g of polyvinyl chloride pellets are then added to this mixture, and the mixture is intimately mixed until it becomes a paste. 20 g of the resultant paste are applied to a metal sheet, using a doctor, in such a way as to give a layer of 0.7 mm thickness. The sheet covered by the paste is then heated to 200° C. for 2 minutes, whereupon the paste gels, giving a plasticized PVC film.

EXAMPLE 20a

A piece of the plasticized PVC film from example 20, dimensions 3×3 cm, is placed on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 20b

A piece of the plasticized PVC film from example 20, dimensions 3×3 cm, is placed on the base of a glass beaker which contains 20 ml of a test microbial suspension of *Pseudomonas aeruginosa*, and is subjected to shaking. After a contact time of 4 hours, 1 ml of the test microbial suspension is removed, and the number of microbes in the test mixture is determined. After expiry of this time, the number of microbes has fallen from $10^7$ to $10^4$ microbes per ml.

EXAMPLE 21

50 ml of dimethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are dissolved in 32 g of diisononyl phthalate. 64 g of polyvinyl chloride pellets are then added to this mixture, and the mixture is intimately mixed until it becomes a paste. 20 g of the resultant paste are applied to a metal sheet, using a doctor, in such a way as to give a layer of 0.7 mm thickness. The sheet covered by the paste is then heated to 200° C. for 2 minutes, whereupon the paste gels, giving a plasticized PVC film.

EXAMPLE 21a

A piece of the plasticized PVC film from example 21, dimensions 3×3 cm, is placed on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 21b

A piece of the plasticized PVC film from example 21, dimensions 3×3 cm, is placed on the base of a glass beaker which contains 20 ml of a test microbial suspension of *Pseudomonas aeruginosa*, and is subjected to shaking. After a contact time of 4 hours, 1 ml of the test microbial suspension is removed, and the number of microbes in the test mixture is determined. After expiry of this time, the number of microbes has fallen from $10^7$ to $10^3$.

EXAMPLE 22

50 ml of diethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are dissolved in 32 g of diisononyl phthalate. 64 g of polyvinyl chloride pellets are then added to this mixture, and the mixture is intimately mixed until it becomes a paste. 20 g of the resultant paste are applied to a metal sheet, using a doctor, in such a way as to give a layer of 0.7 mm thickness. The sheet covered by the paste is then heated to 200° C. for 2 minutes, whereupon the paste gels, giving a plasticized PVC film.

EXAMPLE 22a

A piece of the plasticized PVC film from example 22, dimensions 3×3 cm, is placed on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 22b

A piece of the plasticized PVC film from example 22, dimensions 3×3 cm, is placed on the base of a glass beaker which contains 20 ml of a test microbial suspension of *Pseudomonas aeruginosa*, and is subjected to shaking. After a contact time of 4 hours, 1 ml of the test microbial suspension is removed, and the number of microbes in the test mixture is determined. After expiry of this time, the number of microbes has fallen from $10^7$ to $10^3$.

EXAMPLE 23

50 ml of dimethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 5 g of the product are stirred into 95 g of Rowacryl G-31293 acrylic surface coating from the company ROWA.

EXAMPLE 23a

Using a brush, an aluminum sheet of dimensions 5×5 cm is painted with the acrylic surface coating from example 23 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 23b

Using a brush, an aluminum sheet of dimensions 5×5 cm is painted with the acrylic surface coating from example 23 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^4$.

EXAMPLE 24

45 ml of N-3-dimethylaminopropylacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are stirred into 98 g of Rowacryl G-31293 acrylic surface coating from the company ROWA.

EXAMPLE 24a

Using a brush, an aluminum sheet of dimensions 5×5 cm is painted with the acrylic surface coating from example 24 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 24b

Using a brush, an aluminum sheet of dimensions 5×5 cm is painted with the acrylic surface coating from example 24 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^3$.

EXAMPLE 25

50 ml of dimethylaminopropylmethacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 5 g of the product are stirred into 95 g of Plextol D 510 from the company PolymerLatex, an aqueous dispersion of a methacrylate-acrylate copolymer.

EXAMPLE 25a

Using a brush, an aluminum sheet of dimensions 5×5 cm is painted with the dispersion from example 25 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 25b

Using a brush, an aluminum sheet of dimensions 5×5 cm is painted with the dispersion from example 25 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^4$.

EXAMPLE 26

45 ml of N-3-dimethylaminopropylacrylamide (Aldrich) and 250 ml of ethanol are charged to a three-necked flask and heated to 65° C. under a stream of argon. 0.6 g of azobisisobutyronitrile dissolved in 20 ml of ethyl methyl ketone is then slowly added dropwise, with stirring. The mixture is heated to 70° C. and stirred at this temperature for 72 hours. After expiry of this time, the reaction mixture is stirred into 1.5 l of cyclohexane, whereupon the polymeric product precipitates. After separation of the product by filtration, the filter residue is washed with 100 ml of n-hexane in order to remove any residual monomers still present. The product is then dried in vacuo at 50° C. for 24 hours. 2 g of the product are stirred into 98 g of Plextol D 510 from the company PolymerLatex, an aqueous dispersion of a methacrylate-acrylate copolymer.

EXAMPLE 26a

Using a brush, an aluminum sheet of dimensions 5×5 cm is painted with the dispersion from example 26 and then dried for 24 hours at 35° C. in a drying cabinet. This aluminum sheet is placed, with its coated side upward, on the base of a glass beaker which contains 20 ml of a test microbial suspension of *Staphylococcus aureus*, and is subjected to shaking. After a contact time of 2 hours, 1 ml of the test microbial suspension is removed, and the number of microbes in the test mixture is determined. After expiry of this time, no remaining *Staphylococcus aureus* microbes are detectable.

EXAMPLE 26b

Using a brush, an aluminum sheet of dimensions 5×5 cm is painted with the dispersion from example 26 and then dried for 24 hours at 35° C. in a drying cabinet. This aluminum sheet is placed, with its coated side upward, on the base of a glass beaker which contains 20 ml of a test microbial suspension of *Pseudomonas aeruginosa*, and is subjected to shaking. After a contact time of 2 hours, 1 ml of the test microbial suspension is removed, and the number of microbes in the test mixture is determined. After expiry of this time, the number of microbes has fallen from $10^7$ to $10^3$.

What is claimed is:

1. An antimicrobial polymer blend, characterized in that
one or more antimicrobial polymers each obtainable by polymerizing a monomer of the formula I

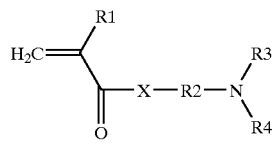

where
R1=—H or —CH₃
R2=branched or unbranched aliphatic hydrocarbon radical having from 1 to 5 carbon atoms,
R3=H, or branched or unbranched aliphatic hydrocarbon radical having from 1 to 7 carbon atoms,
R4=H, or branched or unbranched aliphatic hydrocarbon radical having from 1 to 7 carbon atoms,
R5=H, or branched or unbranched aliphatic hydrocarbon radical having from 1 to 7 carbon atoms, and

X=O,NH,NR5 are mixed with at least one other polymer other than cellulose acetate butyrate and polyesters.

2. The antimicrobial polymer blend as claimed in claim 1, characterized in that the polymer blend is composed of from 0.2 to 90% by weight of one or more antimicrobial polymers.

3. The antimicrobial polymer blend as claimed in claim 1, characterized in that the monomer used of the formula I is 2-tert-butylaminoethyl methacrylate, 2-diethylaminoethyl methacrylate, 2-dimethylaminomethyl methacrylate, 2-tert-butylaminoethyl acrylate, 3-dimethylaminopropyl acrylate, 2-diethylaminoethyl acrylate, 2-dimethylaminoethyl acrylate, N-3-dimethylaminopropylmethacrylamide, N-3-diethylaminopropylmethacrylamide, N-3-dimethylaminopropylacrylamide, or N-3-diethylaminopropylacrylamide.

4. The antimicrobial polymer blend as claimed in claim 2, characterized in that the monomer used of the formula I is 2-tert-butylaminoethyl methacrylate, 2-diethylaminoethyl methacrylate, 2-dimethylaminomethyl methacrylate, 2-tert-butylaminoethyl acrylate, 3-dimethylaminopropyl acrylate, 2-diethylaminoethyl acrylate, 2-dimethylaminoethyl acrylate, N-3-dimethylaminopropylmethacrylamide, N-3-diethylaminopropylmethacrylamide, N-3-dimethylaminopropylacrylamide, or N-3-diethylaminopropylacrylamide.

5. The antimicrobial polymer blend as claimed in claim 1, characterized in that the other polymer used comprises polyurethanes, polyolefins, polyethylene, polypropylene, poly-siloxanes, polystyrene, polyacrylates, polymethylmethacrylate, PVC, polyamides or polyterephthalates.

6. The antimicrobial polymer blend of claim 1, wherein the monomer of formula I comprises acryloyloxyamines (X=O).

7. The antimicrobial polymer blend of claim 1, wherein the monomer of formula I comprises alkylaminoacrylarnides (X=NH).

8. The antimicrobial polymer blend of claim 1, wherein R3 and/or R4 is hydrocarbon.

9. The antimicrobial polymer blend of claim 1, wherein the polymer blend is composed of from 0.2 to 70% by weight of one or more antimicrobial polymers.

10. The antimicrobial polymer blend of claim 1, wherein the polymer blend is composed of from 0.2 to 10% by weight of one or more antimicrobial polymers.

11. The antimicrobial polymer blend of claim 1, wherein the antimicrobial polymers are prepared by free-radical polymerization of monomers of formula I in solution using a free-radical initiator.

* * * * *